United States Patent
Ikeda et al.

(10) Patent No.: US 10,293,026 B2
(45) Date of Patent: May 21, 2019

(54) AGENT FOR PREVENTING OR TREATING DEMYELINATING DISEASE

(71) Applicant: Osaka University, Suita-shi, Osaka (JP)

(72) Inventors: Rieko Ikeda, Suita (JP); Mariko Kuroda, Suita (JP); Toshihide Yamashita, Suita (JP)

(73) Assignee: Osaka University, Osaka (JP)

( * ) Notice: Subject to any disclaimer, the term of this patent is extended or adjusted under 35 U.S.C. 154(b) by 65 days.

(21) Appl. No.: 15/509,777

(22) PCT Filed: Sep. 8, 2015

(86) PCT No.: PCT/JP2015/075473
§ 371 (c)(1),
(2) Date: Mar. 8, 2017

(87) PCT Pub. No.: WO2016/039339
PCT Pub. Date: Mar. 17, 2016

(65) Prior Publication Data
US 2017/0258875 A1  Sep. 14, 2017

(30) Foreign Application Priority Data

Sep. 8, 2014 (JP) ................................ 2014-182551

(51) Int. Cl.
*A61K 38/18* (2006.01)
*C07K 14/50* (2006.01)
*C12N 15/00* (2006.01)
*A61K 31/713* (2006.01)

(52) U.S. Cl.
CPC ........ *A61K 38/1825* (2013.01); *A61K 31/713* (2013.01); *C07K 14/50* (2013.01); *C12N 15/00* (2013.01)

(58) Field of Classification Search
CPC .............. C12N 5/0622; A61K 38/1825; A61K 35/1825
See application file for complete search history.

(56) References Cited

U.S. PATENT DOCUMENTS

| | | |
|---|---|---|
| 2009/0175867 A1 | 7/2009 | Thompson et al. |
| 2012/0165377 A1 | 6/2012 | Takizawa et al. |
| 2013/0102009 A1 | 4/2013 | Dai et al. |
| 2015/0210764 A1 | 7/2015 | Mondal et al. |

FOREIGN PATENT DOCUMENTS

| | | | | |
|---|---|---|---|---|
| JP | 2009539413 A | | 11/2009 | |
| JP | 2013523189 A | | 6/2013 | |
| WO | WO 04/096245 | * | 11/2004 | ............. A61K 35/34 |
| WO | WO 04/105787 | * | 12/2004 | ............. A61K 38/18 |
| WO | WO 2011/037223 A1 | | 3/2011 | |
| WO | WO 2012/066075 A1 | | 5/2012 | |
| WO | WO 2013/033452 A2 | | 3/2013 | |
| WO | WO 2013/173158 A1 | | 11/2013 | |
| WO | WO 2013/188181 A1 | | 12/2013 | |

OTHER PUBLICATIONS

Gauthier et al, "Different functions for the thyroid hormone receptors TRα and TRα in the control of thyroid hormone production and post-natal development." The EMBO Journal, 1999, vol. 18, No. 3, pp. 623-631. (Year: 1999).*
Lovett-Racke et al, "Peroxisome Proliferator-Activated Receptor α Agonists as Therapy for Autoimmune Disease" The Journal of Immunology, 2004, vol. 172, pp. 5790-5798. (Year: 2004).*
Hadjab, et al. 2013 "A local source of FGF initiates development of the unmyelinated lineage of sensory neurons" *Journal of Neuroscience* 33(45): 17656-17666.
Huang, et al. 2013 "The cell adhesion molecule L1 regulates the expression of FGF21 and enhances neurite outgrowth" *Brain Res* 1530: 13-21.
International Search Report in PCT/JP2015/075473, dated Nov. 2, 2015.

* cited by examiner

*Primary Examiner* — Allison M Fox
(74) *Attorney, Agent, or Firm* — Knobbe, Martens, Olson & Bear LLP

(57) ABSTRACT

An object of the present invention is to provide a pharmaceutical preparation that can promote the proliferation of oligodendrocyte precursor cells to effectively prevent or treat a demyelinating disease. FGF21 acts to promote the proliferation of oligodendrocyte precursor cells, and thus, the administration of FGF21, DNA encoding FGF21, an FGF21 production-promoting substance, and/or FGF21-producing cells is effective for preventing or treating a demyelinating disease.

4 Claims, 5 Drawing Sheets
Specification includes a Sequence Listing.

* P<0.05 compared with control. N=4-5. Mean ± SEM.

** P<0.01 compared with control. N=5-6. Mean ± SEM.

Number of days after lysophosphatidylcholine administration

AGENT FOR PREVENTING OR TREATING DEMYELINATING DISEASE

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 25433827_1.TXT, the date of creation of the ASCII text file is Mar. 8, 2017, and the size of the ASCII text file is 3.08 KB.

TECHNICAL FIELD

The present invention relates to an agent for preventing or treating a demyelinating disease. More specifically, the present invention relates to an agent for preventing or treating a demyelinating disease that can promote the proliferation of oligodendrocyte precursor cells to effectively repair the myelin sheath. The present invention also relates to a method for preventing or treating a demyelinating disease.

BACKGROUND ART

A neuron has a neurite extending to contact another neuron, and neuronal function is served by the propagation of neuronal activity through this contact. In the central nervous system composed of the brain and spinal cord, most of neurites are covered with the myelin sheath. The myelin sheath promotes saltatory conduction of neuronal activity to accelerate the propagation of neuronal activity, and also contributes to the maintenance of the homeostasis of axons inside the myelin sheath.

It is known that a breakdown of transmission of neuronal activity due to the removal of myelin sheath causes the appearance of diverse neurological symptoms, leading to the onset of a neurological disease referred to as a demyelinating disease. Demyelinating diseases are broadly classified into two categories: demyelinating diseases of the central nervous system such as multiple sclerosis and acute disseminated encephalomyelitis; and demyelinating diseases of the peripheral nervous system such as Guillain-Barre syndrome and chronic inflammatory demyelinating polyradiculoneuritis. Multiple sclerosis, which is one of the demyelinating diseases of the central nervous system, is characterized by temporal and spatial development of demyelination lesions due to abnormal activation of the autoimmune system. Symptoms that appear include visual disturbances, sensory disturbances, motor dysfunction, and autonomic disturbances. The prevalence of multiple sclerosis in Japan is said to be 8 to 9 in 100,000 people, and there are about 12,000 to 16,000 people affected with multiple sclerosis within the country. Hence, the establishment of a fundamental therapeutic method for a demyelinating disease such as multiple sclerosis is an urgent issue.

It is known that the myelin sheath is formed through the proliferation, migration, and differentiation of oligodendrocyte precursor cells. For the treatment of demyelinating diseases, therefore, it would be effective to repair the removed myelin sheath by promoting the proliferation of oligodendrocyte precursor cells. However, no drug has been previously developed that can promote the proliferation of oligodendrocyte precursor cells, and the treatment of demyelinating diseases mainly involves palliative treatments such as the administration of steroids and immunosuppressants, and rehabilitation. Thus, no fundamental therapeutic method has been established yet.

On the other hand, fibroblast growth factors (FGFs) are known as growth factors involved in neovascularization, wound healing, and cell proliferation. There are 23 subtypes of FGFs; one of the subtypes, FGF21, is highly expressed in the liver and pancreas, and has been shown to have diverse activities such as nutrient intake, lipolysis, glucose metabolism, and biological clock control. Furthermore, in recent years, there has been an attempt to use FGF21 as a therapeutic agent for obesity, diabetes, pancreatitis, dyslipidemia, nonalcoholic steatohepatitis (NASH), insulin resistance, hyperinsulinemia, glucose intolerance, hyperglycemia, metabolic syndrome, and the like (Patent Literature 1, for example). However, an effect of FGF21 on the proliferation of oligodendrocyte precursor cells has been hitherto unknown.

CITATION LIST

Patent Literature

Patent Literature 1: WO 2012/66075

SUMMARY OF INVENTION

Technical Problem

An object of the present invention is to provide a pharmaceutical preparation that can promote the proliferation of oligodendrocyte precursor cells to effectively prevent or treat a demyelinating disease.

Solution to Problem

The present inventors conducted extensive research to solve the aforementioned problem, and found that FGF21 acts to promote the proliferation of oligodendrocyte precursor cells, and thus, the administration of FGF21, DNA encoding FGF21, an FGF21 production-promoting substance, and/or FGF21-producing cells is effective for preventing or treating a demyelinating disease. The present invention was completed by conducting further research based on this finding.

In summary, the present invention provides aspects of invention as itemized below.

Item 1. An agent for preventing or treating a demyelinating disease comprising, as an active ingredient, at least one member selected from the group consisting of FGF21, DNA encoding FGF21, an FGF21 production-promoting substance, and FGF21-producing cells.

Item 2. The agent for preventing or treating a demyelinating disease according to item 1, wherein the active ingredient is FGF21.

Item 3. The agent for preventing or treating a demyelinating disease according to item 1 or 2, wherein the demyelinating disease is a demyelinating disease of the central nervous system.

Item 4. The agent for preventing or treating a demyelinating disease according to any of items 1 to 3, which is used for improving sequelae of the demyelinating disease of the central nervous system.

Item 5. An agent for promoting oligodendrocyte precursor cell proliferation comprising, as an active ingredient, at least one member selected from the group consisting of FGF21, DNA encoding FGF21, an FGF21 production-promoting substance, and FGF21-producing cells.

Item 6. An agent for repairing myelin sheath comprising, as an active ingredient, at least one member selected from the group consisting of FGF21, DNA encoding FGF21, an FGF21 production-promoting substance, and FGF21-producing cells.

Item 7. Use of at least one member selected from the group consisting of FGF21, DNA encoding FGF21, an FGF21 production-promoting substance, and FGF21-producing cells, for the manufacture of an agent for preventing or treating a demyelinating disease.

Item 8. Use of at least one member selected from the group consisting of FGF21, DNA encoding FGF21, an FGF21 production-promoting substance, and FGF21-producing cells, for the manufacture of an agent for promoting oligodendrocyte precursor cell proliferation.

Item 9. Use of at least one member selected from the group consisting of FGF21, DNA encoding FGF21, an FGF21 production-promoting substance, and FGF21-producing cells for the manufacture of an agent for repairing myelin sheath.

Item 10. A method for preventing or treating a demyelinating disease comprising the step of administering, to an individual in need of prevention or treatment of a demyelinating disease, at least one member selected from the group consisting of FGF21, DNA encoding FGF21, an FGF21 production-promoting substance, and FGF21-producing cells, in an amount effective for the prevention or treatment.

Item 11. A method for promoting oligodendrocyte precursor cell proliferation comprising the step of administering, to an individual in need of promotion of oligodendrocyte precursor cell proliferation, at least one member selected from the group consisting of FGF21, DNA encoding FGF21, an FGF21 production-promoting substance, and FGF21-producing cells, in an amount effective for promoting oligodendrocyte precursor cell proliferation.

Item 12. A method for repairing myelin sheath comprising the step of administering, to an individual in need of repair of myelin sheath, at least one member selected from the group consisting of FGF21, DNA encoding FGF21, an FGF21 production-promoting substance, and FGF21-producing cells, in an amount effective for repairing myelin sheath.

Item 13. At least one member selected from the group consisting of FGF21, DNA encoding FGF21, an FGF21 production-promoting substance, and FGF21-producing cells, which is used in a treatment for preventing or treating a demyelinating disease.

Item 14. At least one member selected from the group consisting of FGF21, DNA encoding FGF21, an FGF21 production-promoting substance, and FGF21-producing cells, which is used in a treatment for promoting oligodendrocyte precursor cell proliferation.

Item 15. At least one member selected from the group consisting of FGF21, DNA encoding FGF21, an FGF21 production-promoting substance, and FGF21-producing cells, which is used in a treatment for repairing myelin sheath.

Advantageous Effects of Invention

According to the present invention, a demyelinating disease can be effectively prevented or treated by promoting the proliferation of oligodendrocyte precursor cells that serve to repair the myelin sheath, by augmenting the amount of FGF21 in vivo. Furthermore, according to the present invention, sequelae of a demyelinating disease of the central nervous system can be improved by repairing the myelin sheath. Thus, the present invention has established a technique for promoting the proliferation of oligodendrocyte precursor cells, and can bring benefits to patients with a demyelinating disease, as a fundamental therapy for a demyelinating disease.

DESCRIPTION OF EMBODIMENTS

Figure 1:
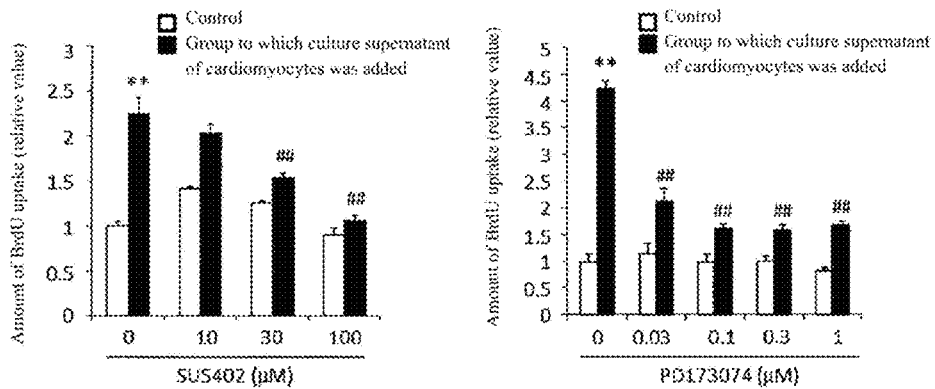
FIG. 1 shows the results of measuring amounts of BrdU uptake by oligodendrocyte precursor cells in Test Example 1.

1. Agent for Preventing or Treating Demyelinating Disease

An agent for preventing or treating a demyelinating disease according to the present invention comprises, as an active ingredient, at least one member selected from the group consisting of FGF21, DNA encoding FGF21, an FGF21 production-promoting substance, and FGF21-producing cells. The present invention will be hereinafter described in detail.

Active Ingredient

In the present invention, at least one member selected from the group consisting of FGF21, DNA encoding FGF21, an FGF21 production-promoting substance, and FGF21-producing cells is used as an active ingredient.

(FGF21)

FGF21 per se promotes the proliferation of oligodendrocyte precursor cells in a living body to which it is administered, and thus, can be used as an active ingredient for preventing or treating a demyelinating disease.

Specific examples of FGF21 used in the present invention include human FGF21, orthologs thereof, and variants thereof.

Human FGF21 is a secreted protein containing a signal sequence consisting of 28 amino acids (the amino acid sequence shown in SEQ ID NO: 1). In the present invention, human FGF21 containing the signal sequence (the amino acid residues at positions 1 to 28 in the amino acid sequence shown in SEQ ID NO: 1) may be used, or human FGF21 devoid of the signal sequence may be used.

Examples of FGF21 orthologs include, but are not particularly limited to, those derived from mammals such as rats, hamsters, guinea pigs, mice, cows, sheep, pigs, goats, monkeys, and rabbits; and birds such as chickens and ostriches. The origin of FGF21 may be decided as appropriate, in accordance with the species of the organism to which FGF21 is to be administered.

FGF21 variants are not particularly limited as long as they possess the inherent biological activity of FGF21, and examples thereof include mutated FGF21 and FGF21 modified using a genetic engineering technique. FGF21 variants have been reported in JP 2011-523561 A, JP 2012-504965 A, JP 2012-525844 A, and JP 2012-525847 A, for example, and these known FGF21 variants may be used in the present invention.

FGF21 may be a native protein or a recombinant manufactured using a genetic engineering technique.

(DNA Encoding FGF21)

The DNA encoding FGF21 expresses FGF21 in a living body to which it is administered, and promotes the proliferation of oligodendrocyte precursor cells, and thus, can be used as an active ingredient for preventing or treating a demyelinating disease.

The base sequence of DNA encoding FGF21 is known, and, for example, DNA encoding human FGF21 is known as the base sequence shown in SEQ ID NO: 2. The DNA encoding FGF21 can be obtained using a genetic engineering technique, based on the base sequence.

The DNA encoding FGF21 is preferably incorporated into an expression vector and used, to enable expression of FGF21 in vivo.

Specific examples of expression vectors include plasmid vectors, adenovirus vectors, adenovirus-associated viral vectors, herpes virus vectors, vaccinia virus vectors, retroviral vectors, lentivirus vectors, and Sendai virus vectors. In particular, a viral vector is preferred for administration to a mammal such as a human.

In such an expression vector, the DNA encoding FGF21 may be functionally linked to a promoter that can demonstrate promoter activity in cells of the living body to which it is to be administered. The promoter used in the expression vector is not particularly limited as long as it can function in the living body to which it is to be administered, and examples thereof include viral promoters such as SV40-derived promoter, cytomegalovirus LTR, Rous sarcoma virus LTR, MoMuLV-derived LTR, and adenovirus-derived promoter; and mammalian constitutive protein gene promoters such as β-actin gene promoter, PGK gene promoter, and transferrin gene promoter.

The expression vector preferably contains a transcription termination signal downstream of the DNA encoding FGF21. Furthermore, the expression vector may additionally contain a selection marker gene for selecting transformants.

(FGF21 Expression-Promoting Substance)

The FGF21 expression-promoting substance is a substance that promotes the expression of FGF21 in vivo. The FGF21 production-promoting substance enhances, in a living body to which it is administered, the ability to express FGF21 inherent in the living body, and the expressed FGF21 promotes the proliferation of oligodendrocyte precursor cells; thus, the FGF21 production-promoting substance can be used as an active ingredient for preventing or treating a demyelinating disease.

The FGF21 expression-promoting substance may act in any stage such as transcription, posttranscriptional control, translation, posttranslational modification, localization, or folding of FGF21, as long as it promotes the expression of FGF21 in vivo.

Specific examples of FGF21 expression-promoting substances include PPARα agonists such as fenofibrate, rosiglitazone, and GW7647; and transcription factors such as CREBH, ATF2, ATF4, PARβ, thyroid hormone receptor β, and ROPα. In the case of a transcription factor, it may be used in a state incorporated into an expression vector, as with DNA.

(FGF21-Producing Cells)

The FGF21-producing cells are cells having the ability to produce FGF21. The FGF21-producing cells produce FGF21 in a living body to which they are administered, and the produced FGF21 promotes the proliferation of oligodendrocyte precursor cells; thus, the FGF21-producing cells can be used as an active ingredient for preventing or treating a demyelinating disease.

The FGF21-producing cells are not particularly limited as long as they have the ability to produce FGF21, and can be administered to a living body; specific examples thereof include in vivo cells such as pancreatic islets, cardiomyocytes, and hepatic cells; transformants in which the DNA encoding FGF21 is incorporated; and differentiated FGF21-producing cells induced from stem cells such as iPS cells.

The FGF21-producing cells used in the present invention are preferably autologous cells obtained from the living body to which they are to be administered, or cells transformed or induced from the autologous cells; however, the FGF21-producing cells may also be heterologous cells obtained from a living body other than the living body to which they are to be administered, or cells transformed or induced from the heterologous cells.

(Suitable Active Ingredients)

In the present invention, at least one member may be selected from FGF21, DNA encoding FGF21, an FGF21 production-promoting substance, and FGF21-producing cells, and used, or a combination of two or more from the above may be used. Among these active ingredients, FGF21 may be preferred, from the standpoint of promoting the proliferation of oligodendrocyte precursor cells even more effectively.

Other Components

The agent for preventing or treating a demyelinating disease of the present invention may contain, in addition to the above-described active ingredients, other pharmacologically active components effective for preventing or treating a demyelinating disease.

The agent for preventing or treating a demyelinating disease of the present invention may also optionally contain, in addition to the above-described active ingredients, pharmacologically acceptable carriers, to be prepared into a desired form of administration and dosage form. Specific examples of pharmacologically acceptable carriers include suspending agents such as methylcellulose, polysorbate 80, hydroxyethyl cellulose, gum arabic, powdered tragacanth, carboxymethylcellulose sodium, and polyoxyethylene sorbitan monolaurate; solubilizers such as polyoxyethylene hardened castor oil, polysorbate 80, nicotinamide, polyoxyethylene sorbitan monolaurate, and Macrogol; stabilizers such as human serum albumin, dextran, methylcellulose, gelatin, sodium sulfite, and sodium metasulfite; adsorption inhibitors such as human serum albumin, lecithin, dextran, ethylene oxide/propylene oxide copolymer, hydroxypropylcellulose, methylcellulose, polyoxyethylene hardened castor oil, and polyethylene glycol; excipients such as sucrose, starch, mannite, sorbit, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrators such as starch, carboxymethyl cellulose, hydroxypropyl starch, sodium bicarbonate, calcium phosphate, and calcium citrate; lubricants such as magnesium stearate; diluents such as water and saline solution; lipids; buffers; emulsifiers; colorants; flavors; and sweeteners.

When a gene encoding FGF21, a transcription factor such as CREBH, or the like is used as an active ingredient in the agent for preventing or treating a demyelinating disease of the present invention, the agent for preventing or treating a demyelinating disease may contain a transfection reagent used in an agent for gene therapy.

Dosage Form

The dosage form of the agent for preventing or treating a demyelinating disease of the present invention is not particularly limited, and may be decided as appropriate, in accordance with the type of the active ingredient used, the form of administration, and the like. Specific examples of dosage forms of the agent for preventing or treating a demyelinating disease of the present invention include liquid preparations such as injections, syrups, cell suspensions, and liposomal preparations; and solid preparations such as tablets, hard capsules, soft capsules, granules, powders, and pills. In the case of an injection, it may be in the form of a powder for preparation before use (freeze-dried powder, for example) that is dissolved in saline solution or the like before use.

Subjects for Administration

The agent for preventing or treating a demyelinating disease of the present invention is used for the purpose of preventing or treating a demyelinating disease, because it can repair the myelin sheath by promoting the proliferation of oligodendrocyte precursor cells. A demyelinating disease is one of neurological diseases that occur due to impairment of the myelin sheath of myelinated nerves.

The demyelinating disease to be prevented or treated in the present invention may be a demyelinating disease of either the central nervous system or peripheral nervous system. Specific examples of demyelinating diseases of the central nervous system to be prevented or treated in the present invention include inflammatory demyelinating diseases such as multiple sclerosis, optic neuromyelitis, acute disseminated encephalomyelitis, and concentric sclerosis; viral demyelinating diseases such as subacute sclerosing panencephalitis and progressive multifocal encephalopathy; toxic demyelinating diseases such as CO intoxication and cerebral hypoxia; metabolic demyelinating diseases such as metachromatic leukodystrophy and adrenoleukodystrophy; central pontine myelinolysis, and vitamin B12 deficiency. Specific examples of demyelinating diseases of the peripheral nervous system to be prevented or treated in the present invention include Guillain-Barre syndrome and chronic inflammatory demyelinating polyradiculoneuritis. Among these demyelinating diseases, the demyelinating disease to be prevented or treated in the present invention may be preferably a demyelinating disease of the central nervous system, more preferably an inflammatory demyelinating disease of the central nervous system, and still more preferably multiple sclerosis.

Furthermore, the agent for preventing or treating a demyelinating disease of the present invention, when administered to a patient with sequelae of a demyelinating disease of the central nervous system, can improve the sequelae by repairing the myelin sheath.

The organism to which the agent for preventing or treating a demyelinating disease of the present invention is to be administered may be an organism affected with a demyelinating disease, and examples thereof include, in addition to humans, mammals such as rats, hamsters, guinea pigs, mice, cows, sheep, pigs, goats, monkeys, and rabbits; and birds such as chickens and ostriches. The origin of the active ingredient used in the present invention may be decided as appropriate, in accordance with the type of the organism to which the active ingredient is to be administered. For example, in the case of preventing or treating a demyelinating disease in a human, an active ingredient may be selected from human FGF21, DNA encoding human FGF21, a human FGF21 production-promoting substance, and human-derived cells producing human FGF21, and the like, and used.

Method of Administration

Examples of forms of administration of the agent for preventing or treating a demyelinating disease of the present invention include oral administration, topical administration, subcutaneous administration, intraperitoneal administration, intramuscular administration, intravenous administration, transrectal administration, and intracutaneous administration, and the form of administration may be decided as appropriate, in accordance with the type of the active ingredient used. Among these forms of administration, topical administration may be preferred for preventing or treating a demyelinating disease according to the present invention.

The dose of the agent for preventing or treating a demyelinating disease of the present invention may be decided as appropriate, to provide an amount effective for preventing or treating a demyelinating disease, in accordance with the type of the active ingredient used, the age, sex, body weight, or degree of symptoms of the subject to which the agent is to be administered, the form of administration, and the like. For example, when FGF21 is used as the active ingredient, a dose of about 0.1 to 10 µg, preferably about 1 to 5 µg, per day, may be administered in single or divided doses. When the DNA encoding FGF21, the FGF21 production-promoting substance, and/or the FGF21-producing cells is used as the active ingredient, the dose thereof may be decided as appropriate, such that the amount of FGF21 produced in vivo is within the above-described range.

2. Agent for Promoting Oligodendrocyte Precursor Cell Proliferation and Agent for Repairing Myelin Sheath The above-described active ingredient promotes the proliferation of oligodendrocyte precursor cells, and thus, can also be used as an agent for promoting oligodendrocyte precursor cell proliferation. Furthermore, the above-described active ingredient can repair removed myelin sheath by promoting the proliferation of oligodendrocyte precursor cells, and thus, can also be used as an agent for repairing myelin sheath.

That is, the present invention further provides an agent for promoting oligodendrocyte precursor cell proliferation comprising, as an active ingredient, at least one member selected from the group consisting of FGF21, DNA encoding FGF21, an FGF21 production-promoting substance, and FGF21-producing cells. The present invention also provides an agent for repairing myelin sheath comprising, as an active ingredient, at least one member selected from the group consisting of FGF21, DNA encoding FGF21, an FGF21 production-promoting substance, and FGF21-producing cells.

In the agent for promoting oligodendrocyte precursor cell proliferation and the agent for repairing myelin sheath, the type of the active ingredient, other components that can be optionally incorporated, the dosage form, the subject for administration, the method of administration, and the like are the same as those described in "1. Agent for Preventing or Treating Demyelinating Disease" above.

EXAMPLES

The present invention will be hereinafter described in more detail with reference to examples, which are not intended to limit the present invention.

Example 1: Study of the Involvement of FGF Receptors in the Effect of Proliferating Oligodendrocyte Precursor Cells by Culture Supernatant of Cardiomyocytes A study was conducted to determine whether culture supernatant of cardiomyocytes that produce various growth factors proliferates oligodendrocyte precursor cells, and the action of an FGF receptor antagonist on the proliferation effect was also studied.

(1) Materials and Method

Hearts extracted from C57BL/6j mice (postnatal day 1-old) were minced, and then poured into 1 mg/ml of Type 1 collagenase (Worthington) and shaken at 37° C. for 20 minutes. The obtained cell suspension was pipetted and allowed to stand, and then the supernatant was collected. Remaining cardiomyocytes after the collection of the supernatant were again poured into 1 mg/ml of Type 1 collagenase (Worthington) and shaken at 37° C. for 20 minutes, and then the supernatant was collected. This operation was repeated three times. The collected supernatant was suspended in MEM (modified Eagle's medium) containing 5% calf serum, and the cell suspension was poured into a culture dish. After 30 minutes, suspension cells were collected, and were resuspended in MEM containing 5% calf serum and then centrifuged (2000 rpm, 6 minutes). Thereafter, the precipitate was suspended in MEM containing 5% calf serum, and then cardiomyocytes were separated using the Percoll method. The obtained cardiomyocytes were subsequently seeded in a culture dish and cultured for 2 days in MEM containing 5% calf serum, and the culture supernatant was collected. The obtained culture supernatant of cardiomyocytes was used in the following experiment.

Oligodendrocyte precursor cells were harvested from C57BL/6j mice (postnatal day 1-old) brains, in accordance with the following procedures. Initially, cortices isolated from the C57BL/6j mice were dispersed to form a single-cell state using the Neuronal dissociation kit (Miltenyi) to obtain a cell suspension. The obtained cell suspension was reacted with anti-A2B5 binding beads (Miltenyi), and only the oligodendrocyte precursor cells (A2B5 positive cells) were harvested. A2B5 is a marker for oligodendrocyte precursor cells.

The harvested oligodendrocyte precursor cells were seeded in a poly-L-lysine (Sigma)-coated plastic tissue culture dish, and cultured in a medium for 1 day (37° C., 5% $CO_2$). The medium used was DMEM containing 4 mM L-gludamine (Sigma), 1 mM sodium pyruvate (Sigma), 0.1% bovine serum albumin (Sigma), 50 µg/ml apo-Transferrin (Sigma), 5 µg/ml insulin (Sigma), 30 nM sodium selenite (Sigma), 10 nM biotin (Sigma), 10 nM hydrocortisone (Sigma), 10 ng/ml Platelet-Derived Growth Factor-AA (Peprotech), and 10 ng/ml basic fibroblast growth factor (Peprotech). Thereafter, the culture medium of oligodendrocyte precursor cells was removed, the culture supernatant of cardiomyocytes obtained above was added at 100 wt %, and additionally, SU5402 (Sigma) as an FGFR inhibitor was added at 0 µM, 10 µM, 30 µM, and 100 µM, or PD173074 (Sigma) as an FGFR3 inhibitor was added at 0 µM, 0.03 µM, 0.1 µM, 0.3 µM, and 1 µM, and then the cells were cultured at 37° C. for 24 hours. Bromodeoxyuridine (BrdU) was subsequently added and cultured at 37° C. for 24 hours, and then the cells were collected; the BrdU uptake was then detected using the cell proliferation ELISA, BrdU colorimetric kit (Roche). As a control, the BrdU uptake was measured under the same conditions as those described above, except that the culture supernatant of cardiomyocytes was not added. This experiment studied five or six cases for each group.

(2) Results

FIG. 1 shows the mean±standard error for the results of measuring amounts of BrdU uptake for each group. The amounts of BrdU uptake for each group were statistically analyzed using analysis of variance.

As is clear from FIG. 1, in the group to which the culture supernatant of cardiomyocytes was added, the BrdU uptake by oligodendrocyte precursor cells increased, and the increase in the BrdU uptake was suppressed by the treatment with SU5402 or PD173074. Moreover, a significant difference ($p<0.01$) was observed between the group to which the culture supernatant of cardiomyocytes was added and the group without the culture supernatant of cardiomyocytes (control).

That is, the results of this experiment suggested that the culture supernatant of cardiomyocytes contained a growth factor that promoted the proliferation of oligodendrocyte precursor cells. The results also indicated that the effect of proliferating oligodendrocyte precursor cells by the culture supernatant of cardiomyocytes was mediated by FGF receptors.

Example 2: Identification of the Subtype of FGFs Involved in the Effect of Proliferating Oligodendrocyte Precursor Cells Produced by the Myocardium A study was conducted to determine which subtype of the FGFs contained in the culture supernatant of cardiomyocytes was involved in promoting the proliferation of oligodendrocyte precursor cells.

(1) Materials and Method

Culture supernatant of cardiomyocytes was prepared as in Example 1, using C57BL/6j mice (postnatal day 1-old). Oligodendrocyte precursor cells were harvested from C57BL/6j mice (postnatal day 1-old) brains as in Example 1. The obtained oligodendrocyte precursor cells were divided into four groups, i.e., a group to which an FGF1 neutralizing antibody was added, a group to which an FGF2 neutralizing antibody was added, a group into which FGF18 siRNA was transfected, and a group into which FGF21 siRNA was transfected, and the following experiment was conducted. This experiment studied four cases for each group.

For the group to which an FGF1 neutralizing antibody was added, initially, the oligodendrocyte precursor cells were seeded in a poly-L-lysinde (Sigma)-coated plastic tissue culture dish, and cultured in the following medium for 1 day (37° C., 5% $CO_2$). The medium used was DMEM containing 4 mM L-glutamine (Sigma), 1 mM sodium pyruvate (Sigma), 0.1% bovine serum albumin (Sigma), 50 µg/ml apo-Transferrin (Sigma), 5 µg/ml insulin (Sigma), 30 nM sodium selenite (Sigma), 10 nM biotin (Sigma), 10 nM hydrocortisone (Sigma), 10 ng/ml Platelet-Derived Growth Factor-AA (Peprotech), and 10 ng/ml basic fibroblast growth factor (Peprotech). Thereafter, the culture medium of oligodendrocyte precursor cells was removed, the culture supernatant of cardiomyocytes obtained above was added at 100 wt %, and simultaneously, an FGF1 neutralizing antibody (IgG; R&D) was added at 3 µg/ml and 10 µg/ml, and the cells were cultured at 37° C. for 24 hours. BrdU was subsequently added and cultured at 37° C. for 24 hours, and then the cells were collected; the BrdU uptake was then detected using the cell proliferation ELISA, BrdU colorimetric kit (Roche). As controls, the BrdU uptake was also measured under the same conditions as those described above, for the case where the culture supernatant of cardiomyocytes was not added, and the case where a control IgG (Sigma; 15256) was used instead of the FGF1 neutralizing antibody.

For the group to which an FGF2 neutralizing antibody was added, the experiment was conducted under the same conditions as those described above for the group to which the FGF1 neutralizing antibody was added, except that an FGF2 neutralizing antibody (IgG; Millipore) was used instead of the FGF1 neutralizing antibody. As controls, the BrdU uptake was also measured under the same conditions as those described above, for the case where the culture supernatant of cardiomyocytes was not added, and the case where a control IgG (Sigma; 15256) was used instead of the FGF2 neutralizing antibody.

For the group to which FGF18 siRNA was added, initially, FGF18 siRNA (Life Technologies) was transfected into cardiomyocytes using Lipofectamin RNAi/MAX (Invitrogen). The oligodendrocyte precursor cells were subsequently seeded in a poly-L-lysinde (Sigma)-coated plastic tissue culture dish, and cultured in the following medium for 1 day (37° C., 5% $CO_2$). The medium used was DMEM containing 4 mM L-gludamine (Sigma), 1 mM sodium pyruvate (Sigma), 0.1% bovine serum albumin (Sigma), 50 µg/ml apo-Transferrin (Sigma), 5 µg/ml insulin (Sigma), 30 nM sodium selenite (Sigma), 10 nM biotin (Sigma), 10 nM hydrocortisone (Sigma), 10 ng/ml Platelet-Derived Growth Factor-AA (Peprotech), and 10 ng/ml basic fibroblast growth factor (Peprotech). Thereafter, the culture medium of oligodendrocyte precursor cells was removed, the culture supernatant of cardiomyocytes obtained above was added at 100 wt %, and the cells were cultured at 37° C. for 24 hours. BrdU was subsequently added and cultured at 37° C. for 24 hours, and then the cells were collected; the BrdU uptake was then detected using the cell proliferation ELISA, BrdU colorimetric kit (Roche). As controls, the BrdU uptake was also measured under the same conditions as those described above, for the case where the culture supernatant of cardiomyocytes was not added, the case where FGF18 siRNA was not transfected into cardiomyocytes, and the case where a control siRNA (Applied Biosystem; Silencer select control siRNA) was used instead of FGF18 siRNA.

For the group to which FGF21 siRNA was added, the experiment was conducted under the same conditions as those described above for the group to which FGF18 siRNA was added, except that FGF21 siRNA (Life Technologies) was used instead of FGF18 siRNA. As controls, the BrdU uptake was also measured under the same conditions as those described above, for the case where the culture supernatant of cardiomyocytes was not added, and the case where a control siRNA (Applied Biosystem; Silencer select control siRNA) was used instead of FGF21 siRNA.

(2) Results

Figure 2:
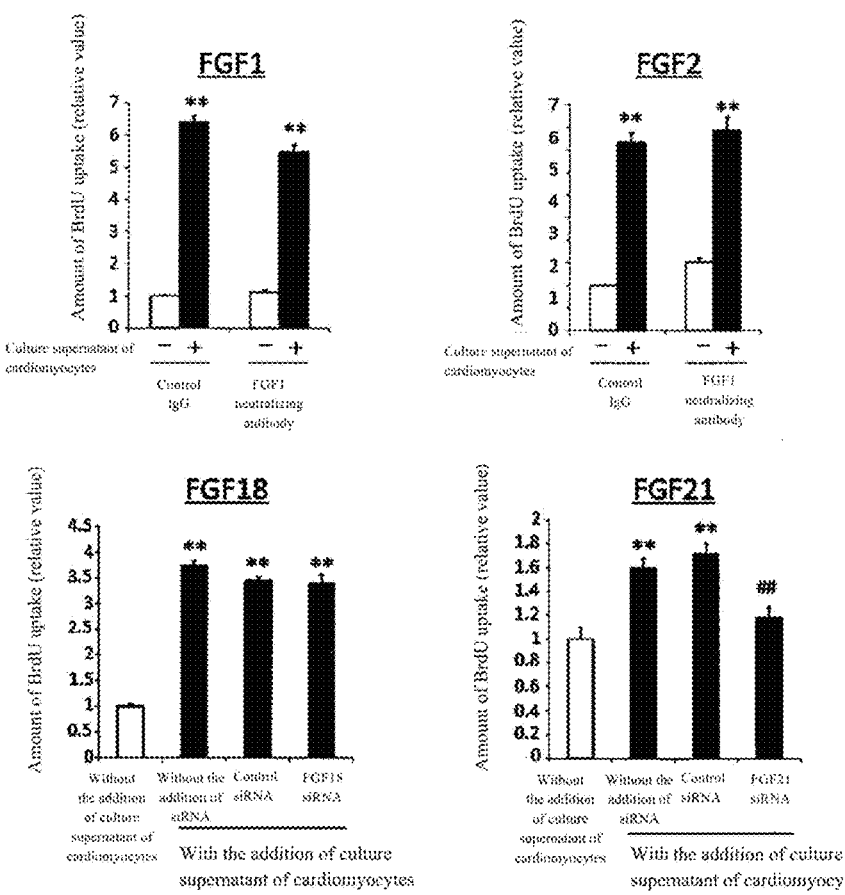
FIG. 2 shows the results of measuring amounts of BrdU uptake by oligodendrocyte precursor cells in Test Example 2.

FIG. 2 shows the mean±standard error for the results of measuring amounts of BrdU uptake for each group. The amounts of BrdU uptake for each group were statistically analyzed using analysis of variance. As is clear from FIG. 2, the BrdU uptake was markedly increased by the addition of the culture supernatant of cardiomyocytes, and the increase in the BrdU uptake through the addition of the culture supernatant of cardiomyocytes was not suppressed in the group to which the FGF1 neutralizing antibody was added, the group to which the FGF2 neutralizing antibody was added, and the group into which FGF18 siRNA was transfected. On the contrary, the increase in the BrdU uptake was significantly suppressed ($p<0.01$) in the group to which FGF21 siRNA was transfected, compared to the case where FGF21 siRNA was not transfected and the case where the control siRNA was used, under the conditions in which the culture supernatant of cardiomyocytes was added.

The foregoing results suggested that FGF1, FGF2, and FGF18 do not have an effect on the proliferation of oligodendrocyte precursor cells, whereas FGF21 is involved in promoting the proliferation of oligodendrocyte precursor cells.

Example 3: Study of the Proliferation-Promoting Action of FGF21 on Oligodendrocyte Precursor Cells The proliferation-promoting action of FGF21 on oligodendrocyte precursor cells was verified using cultured cells.

(1) Materials and Method

Recombinant FGF15 (Abcam), FGF21 (R&D), or FGF23 (R&D) was diluted in saline solution immediately before use to prepare an each FGF-containing solution. Oligodendrocyte precursor cells were harvested from C57BL/6j mice (postnatal day 1-old) brains, as in Example 1.

Initially, the oligodendrocyte precursor cells were seeded in a poly-L-lysinde (Sigma)-coated plastic tissue culture dish, and cultured in the following medium for 1 day (37° C., 5% $CO_2$). The medium used was DMEM containing 4 mM L-gludamine (Sigma), 1 mM sodium pyruvate (Sigma), 0.1% bovine serum albumin (Sigma), 50 µg/ml apo-Transferrin (Sigma), 5 µg/ml insulin (Sigma), 30 nM sodium selenite (Sigma), 10 nM biotin (Sigma), 10 nM hydrocortisone (Sigma), 10 ng/ml Platelet-Derived Growth Factor-AA (Peprotech), and 10 ng/ml basic fibroblast growth factor (Peprotech). Thereafter, each type of FGF-containing solution was added to the culture medium of oligodendrocyte precursor cells such that the concentration of each type of FGF was 10 ng/ml, 30 ng/ml, or 100 ng/ml, and the cells were cultured at 37° C. for 24 hours. BrdU was subsequently added and cultured at 37° C. for 24 hours, and then the cells were collected; the BrdU uptake was then detected using the cell proliferation ELISA, BrdU colorimetric kit (Roche). As a control, an equivalent amount of saline solution was used instead of the FGF21-containing solution, and the BrdU uptake was measured under the same conditions as those described above. This experiment studied three cases for each group.

(2) Results

Figure 3:
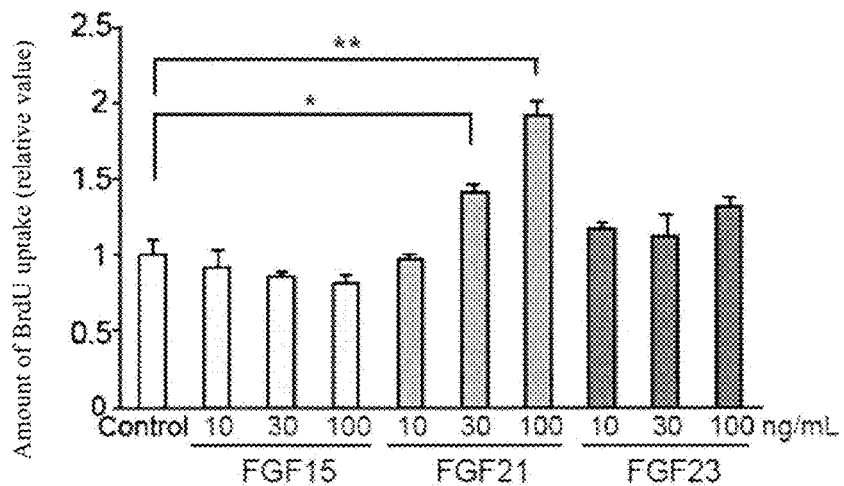
FIG. 3 shows the results of measuring amounts of BrdU uptake by oligodendrocyte precursor cells in Test Example 3.

FIG. 3 shows the mean±standard error for the results of measuring amounts of BrdU uptake for each group. The amounts of BrdU uptake for each group were statistically analyzed. As is clear from FIG. 3, the BrdU uptake by the oligodendrocyte precursor cells was markedly increased by the addition of FGF21, and a significant difference in the amounts of BrdU uptake was observed between the group to which FGF21 was added and the control (to which saline solution was added). A significant difference in the amounts of BrdU uptake was not observed between the group to which FGF15 or FGF23 was added and the control. That is, these results confirmed that FGF21 acts to promote the proliferation of oligodendrocyte precursor cells.

Example 4: Study of the Effect on the Proliferation of Oligodendrocyte Precursor Cells in Demyelination Model Mice (1)

The proliferation-promoting action of FGF21 on oligodendrocyte precursor cells was studied using demyelination model mice.

(1) Materials and Method

Demyelination model mice were produced by topically administering 2 µl per mouse of lysophosphatidylcholine diluted to 1% (w/v) in saline solution into the spinal cord of C57BL/6j mice (female, 7-week-old).

Osmotic pumps (ALZET) were filled with an FGF21-containing solution prepared by diluting recombinant FGF21 (R&D) to 4.17 µg/ml in saline solution, a cannula was attached to the tip of each pump, and the tip was attached to the site of lysophosphatidylcholine administration in each demyelination model mouse to continuously administer FGF21. After 7 days, the demyelination model mice were anesthetized and transcardially perfused with saline solution, and spinal cord tissue was harvested. Ultimately, 350 ng of FGF21 was administered. The spinal cord tissue was fixed with a 4% paraformaldehyde solution, which was then replaced with a 30% sucrose solution, and subsequently, frozen thin sections were prepared. The sections were immunostained using an anti-PDGFRα antibody and an anti-Ki67 antibody, and the number of PDGFRα and Ki67 double-positive cells in the sections was counted. PDGFRα is a marker for oligodendrocyte precursor cells, and Ki67 is a cell proliferation marker. As a control, saline solution was used, and the number of PDGFRα and Ki67 double-positive cells was counted under the same conditions as those described above. This experiment conducted the study using five mice for each group.

(2) Results

Figure 4:
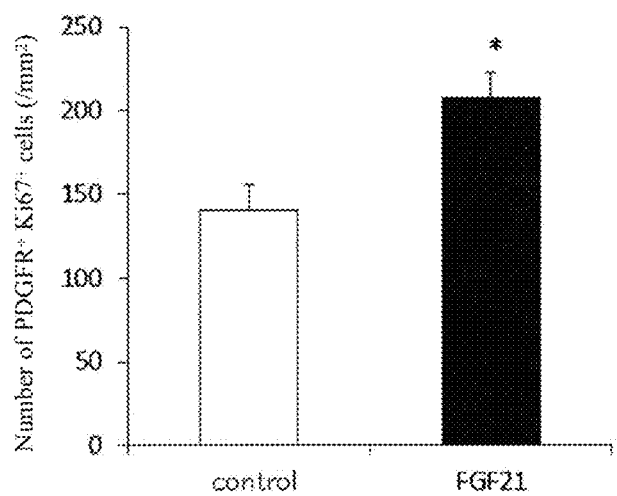
FIG. 4 shows the results of counting the number of PDGFRα and Ki67 double-positive cells in spinal cord tissue in demyelination model mice in Test Example 4.

FIG. 4 shows the mean±standard error for the results of counting the number of PDGFRα and Ki67 double-positive cells. The number of PDGFRα and Ki67 double-positive cells was statistically analyzed using analysis of variance. As shown in FIG. 4, the number of PDGFRα and Ki67 double-positive cells increased in the demyelination model mice to which FGF21 was administered, and a significant difference ($p<0.05$) in the number of PDGFRα and Ki67 double-positive cells was observed between the group to which FGF21 was added and the control (to which saline solution was added). These results revealed that FGF21 can promote the proliferation of oligodendrocyte precursor cells in vivo.

Example 5: Study of the Effect on the Proliferation of Oligodendrocyte Precursor Cells in Demyelination Model Mice The proliferation-promoting action of FGF21 on oligodendrocyte precursor cells was studied using demyelination model mice.

(1) Materials and Method

Demyelination model mice were produced by performing a laminectomy at the 11th and 12th thoracic vertebrae in C57BL/6j mice (female, 7-week-old), and topically administering 2 µl of lysophosphatidylcholine diluted to 1% (w/v) in saline solution at a depth of 2 mm into the midline of the spinal column.

An FGF21-containing solution prepared by diluting recombinant FGF21 (R&D) in saline solution was subcutaneously administered for 2 weeks at a dose of 500 ng/kg body weight of FGF21 per day. After 2 weeks, the demyelination model mice were anesthetized and transcardially perfused with saline solution, and spinal cord tissue was harvested. The harvested spinal cord tissue was fixed with a 4% paraformaldehyde solution, which was then replaced with a 30% sucrose solution, and subsequently, frozen thin sections were prepared. The sections were immunostained using an anti-PDGFRα antibody and an anti-Ki67 antibody, and the number of PDGFRα and Ki67 double-positive cells in the sections was counted. As a control, a saline solution containing 0.5% BSA was used, and the number of PDGFRα and Ki67 double-positive cells was counted under the same conditions as those described above. This experiment conducted the study using five or six mice for each group.

(2) Results

Figure 5:
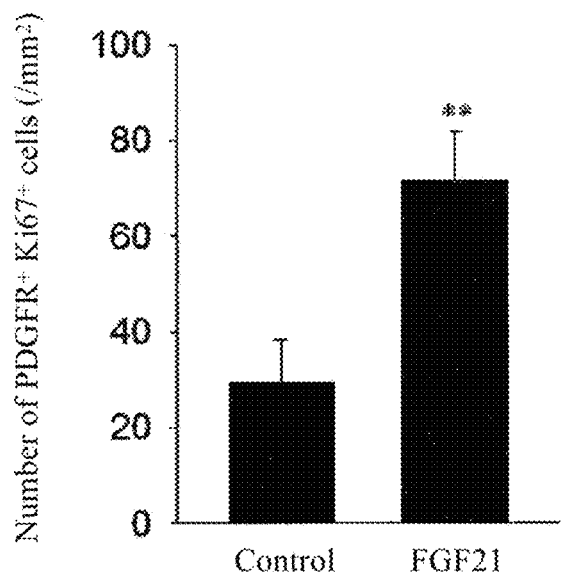
FIG. 5 shows the results of counting the number of PDGFRα and Ki67 co-positive cells in spinal cord tissue in demyelination model mice in Test Example 5.

FIG. 5 shows the mean±standard error for the results of counting the number of PDGFRα and Ki67 double-positive cells. In this experiment as well, the number of PDGFRα and Ki67 double-positive cells increased in the demyelination model mice to which FGF21 was administered, revealing that FGF21 can promote the proliferation of oligodendrocyte precursor cells in vivo.

Example 6: Study of the Effect on Myelin Sheath Repair in Demyelination Model Mice The myelin sheath-repairing action of FGF21 was studied using demyelination model mice.

(1) Materials and Method

Demyelination model mice were created as in Example 5 above. An FGF21-containing solution prepared by diluting recombinant FGF21 (R&D) in saline solution was subcutaneously administered for 2 weeks at a dose of 500 ng/kg body weight of FGF21 per day, to the demyelination model mice after 7 days from the administration of lysophosphatidylcholine. After 2 weeks, the demyelination model mice were anesthetized and transcardially perfused with saline solution, and spinal cord tissue was harvested. Sections were prepared from the harvested spinal cord tissue as in Example 5 above and then immunostained using an anti-MBP antibody, and MBP positive regions in the sections were counted. As a control, a saline solution containing 0.5% BSA was used, and MBP positive regions were counted under the same conditions as those described above. This experiment conducted the study using one mouse for each group.

(2) Results

Figure 6:
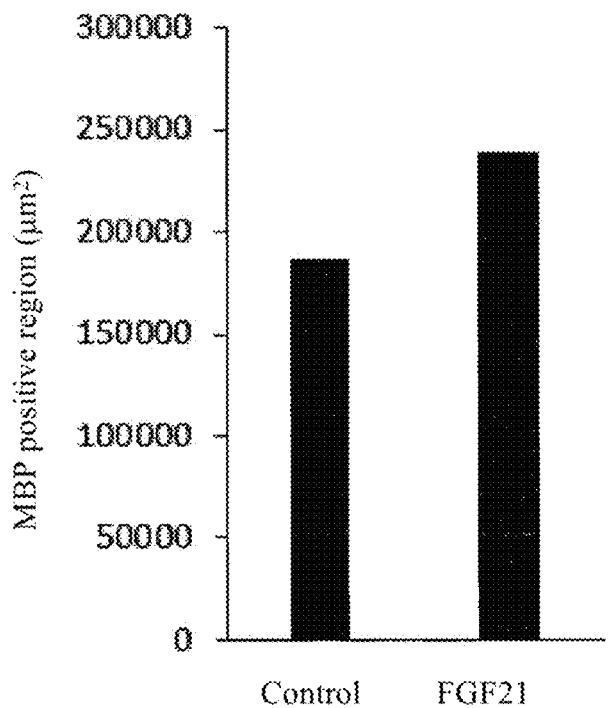
FIG. 6 shows the results of counting MBP positive regions in spinal cord tissue in demyelination model mice in Test Example 5.

FIG. 6 shows the mean for the results of measuring MBP positive regions. MBP positive regions were increased in the demyelination model mice to which FGF21 was administered, revealing that FGF21 can promote myelin sheath repair in vivo.

Example 7: Study of the Effect on Neurological Symptoms in Demyelination Model Mice The therapeutic effect of FGF21 on neurological symptoms was studied using demyelination model mice.

(1) Materials and Method

Demyelination model mice were created, and recombinant FGF21 was administered, as in Example 5 above. The hindlimb motor function of the mice was examined by performing the ladder walk test. A 1-m long ladder was installed in a position at a height of 15 cm. The mice were allowed to walk on the ladder with random widths of 0.6, 1.2, and 1.8 cm. The number of missed steps was counted, and the proportion (%) of the number of missed steps relative to the total number of steps was calculated. This experiment conducted the study using three mice for each group.

(2) Results

Figure 7:
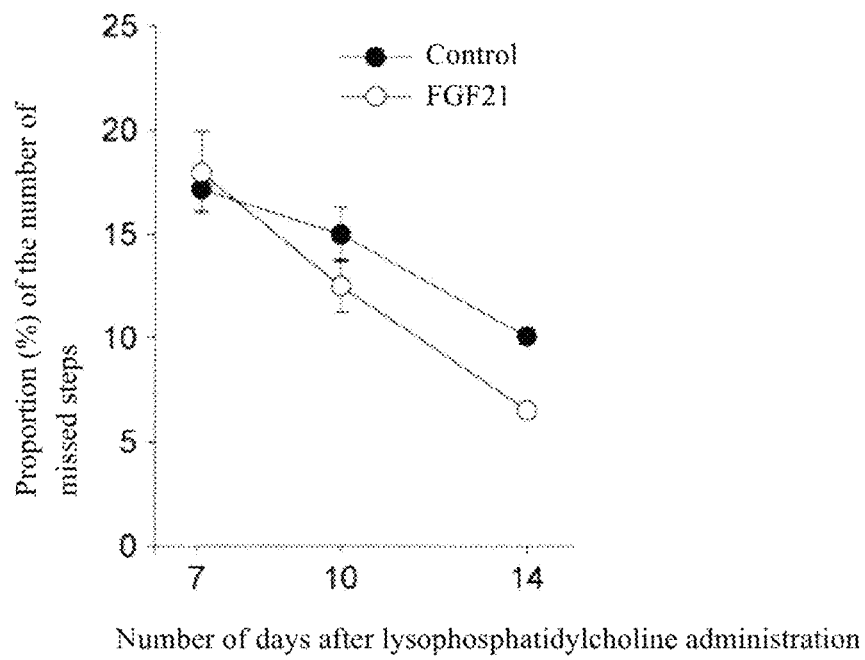
FIG. 7 shows the results of analyzing the hindlimb motor function of demyelination model mice in Test Example 5.

FIG. 7 shows the mean±standard error for the results of calculating the proportion of the number of missed steps on the ladder. The number of missed steps on the ladder decreased in the demyelination model mice to which FGF21 was administered, revealing that FGF21 promotes improvement of neuronal function.

Example 8: Study of the Proliferation-Promoting Action of FGF21 on Human Oligodendrocyte Precursor Cells The proliferation-promoting action of FGF21 on oligodendrocyte precursor cells was verified using human-derived cultured cells.

(1) Materials and Method

Recombinant human FGF21 (R&D) was diluted in saline solution immediately before use to prepare an FGF21-containing solution. Human oligodendrocyte precursor cells (ScienCell) were also prepared.

Initially, the oligodendrocyte precursor cells were seeded in a poly-L-lysinde-coated plastic tissue culture dish (Greiner Bio-One), and cultured in the following medium for 1 day (37° C., 5% $CO_2$). The medium used was DMEM containing 4 mM L-gludamine (Sigma), 1 mM sodium pyruvate (Sigma), 0.1% bovine serum albumin (Sigma), 50 μg/ml apo-Transferrin (Sigma), 5 μg/ml insulin (Sigma), 30 nM sodium selenite (Sigma), 10 nM biotin (Sigma), 10 nM hydrocortisone (Sigma), 10 ng/ml Platelet-Derived Growth Factor-AA (Peprotech), 10 ng/ml basic fibroblast growth factor (Peprotech) 1 (v/v) %, and penicillin/streptomycin (Life Technologies). Thereafter, the FGF21-containing solution was added to the culture medium of oligodendrocyte precursor cells such that the concentration of FGF21 was 6 g/ml, and the cells were cultured at 37° C. for 24 hours. BrdU was subsequently added and cultured at 37° C. for 24 hours, and then the cells were collected; the BrdU uptake was then detected using the cell proliferation ELISA, BrdU colorimetric kit (Roche). As a control, an equivalent amount of saline solution was used instead of the FGF21-containing solution, and the BrdU uptake was measured under the same conditions as those described above. This experiment studied six cases for the control group, and four cases for the FGF21 group.

(2) Results

Figure 8:
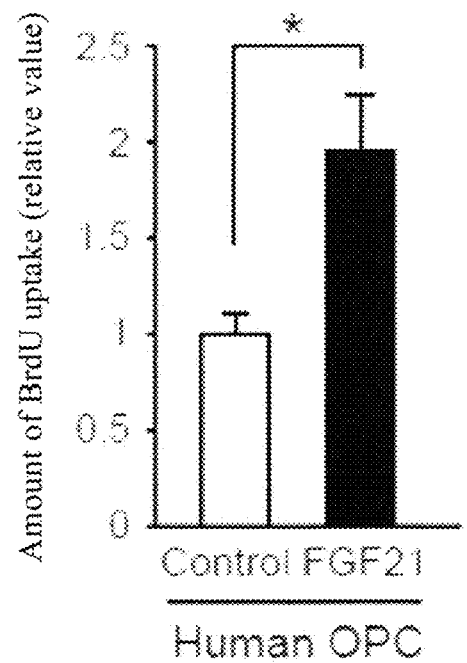
FIG. 8 shows the results of measuring amounts of BrdU uptake by human oligodendrocyte precursor cells in Test Example 6.

FIG. 8 shows the mean±standard error for the results of measuring amounts of BrdU uptake for each group. The amounts of BrdU uptake for each group were statistically analyzed. As is clear from FIG. 8, the BrdU uptake by the oligodendrocyte precursor cells was markedly increased by the addition of FGF21, and a significant difference in the amounts of BrdU uptake was observed between the group to which FGF21 was added and the control (to which saline solution was added). That is, these results confirmed that FGF21 acts to promote the proliferation of human oligodendrocyte precursor cells.

Example 9: Study of the Effect on the Proliferation of Oligodendrocyte Precursor Cells in Brain Contusion Model Mice The proliferation-promoting action of FGF21 on oligodendrocyte precursor cells was studied using brain contusion model mice.

(1) Materials and Method

Anesthetized C57BL/6j mice (female, 7-week-old) were fixed onto a brain stereotaxic apparatus (Narishige). A midline incision was made in the scalp, the fascia was removed, and the skull was exposed. A craniotomy was performed through a 4-mm diameter circle centered at 2 mm lateral to the bregma. A 3-mm diameter chip was connected to the Pneumatic Impact Device (AmScien Instruments) to create a brain contusion. The parameters for imparting impact were as follows: speed: 4 to 4.5 mm/sec, depth: 1 mm, and duration: 120 msec.

Osmotic pumps (ALZET) were filled with an FGF21-containing solution prepared by diluting recombinant FGF21 (R&D) in saline solution. A cannula was attached to the tip of each osmotic pump, and the cannula tip was further connected to a Brain infusion kit (ALZET) to continuously administer the FGF21-containing solution into the ventricles. The FGF21-containing solution was administered for 1 week at a dose of 50 ng/kg body weight of FGF21 per day. Thereafter, the brain contusion mice were anesthetized and transcardially perfused with saline solution, and brain tissue was harvested. The harvested brain tissue was fixed with a 4% paraformaldehyde solution, which was then replaced with a 30% sucrose solution, and subsequently, frozen thin sections were prepared. The sections were immunostained using an anti-PDGFRα antibody and an anti-Ki67 antibody, and the number of PDGFRα and Ki67 double-positive cells in the sections was counted. As a control, a saline solution containing 0.5% BSA (Vehicle) was used, and the number of PDGFRα and Ki67 double-positive cells was counted under the same conditions as those described above. This experiment conducted the study using five or six mice for each group.

(2) Results

Figure 9:
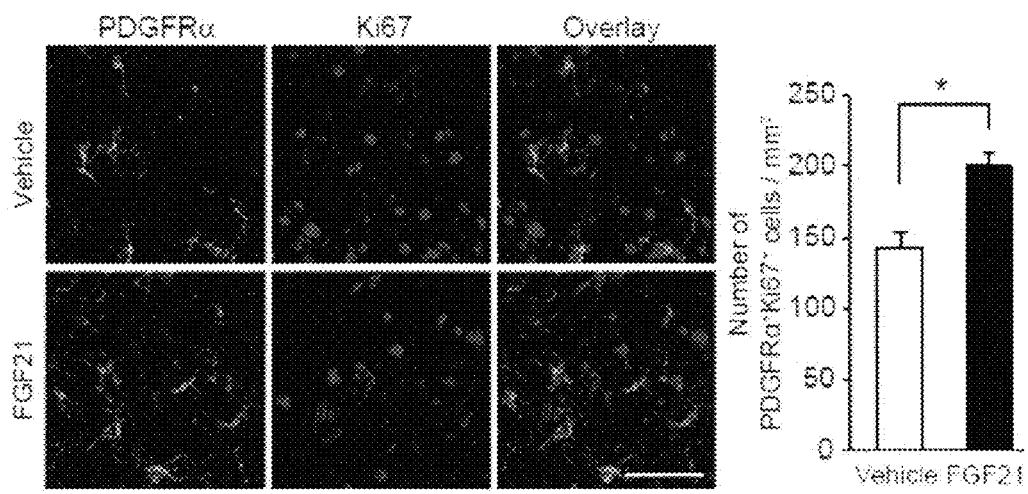
FIG. 9 shows the results of counting the number of PDGFRα and Ki67 double-positive cells in brain tissue in brain contusion model mice in Test Example 9.

FIG. 9 shows the mean±standard error for the results of counting the number of PDGFRα and Ki67 double-positive cells. In this experiment as well, the number of PDGFRα and Ki67 double-positive cells increased in the brain contusion model mice to which FGF21 was administered, revealing that FGF21 can promote the proliferation of oligodendrocyte precursor cells even after brain contusion.

The invention claimed is:

1. A method for treating a demyelinating disease comprising:
   identifying an individual as having a demyelinating disease, and
   administering to the individual as an active ingredient FGF21 in an amount effective for the treatment.

2. The method according to claim 1, wherein the demyelinating disease is a demyelinating disease of the central nervous system.

3. The method according to claim 1, wherein sequelae of the demyelinating disease are improved.

4. A method for repairing myelin sheath comprising:
   identifying an individual as being in need of repair of myelin sheath, and
   administering, to the individual as an active ingredient FGF21 in an amount effective for repairing myelin sheath.

* * * * *

SEQUENCE LISTING

<160> NUMBER OF SEQ ID NOS: 2

<210> SEQ ID NO 1
<211> LENGTH: 209

<212> TYPE: PRT
<213> ORGANISM: Homo sapiens

<400> SEQUENCE: 1

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 2
<211> LENGTH: 630
<212> TYPE: DNA
<213> ORGANISM: Homo sapiens

<400> SEQUENCE: 2

```
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc gaaagtctc     240 ctgcagctga aagccttgaa gccgggagtt attcaaatct gggagtcaa gacatccagg      300 ttcctgtgcc agcggccaga tggggccctg tatggatcgc tccactttga ccctgaggcc     360
tgcagcttcc gggagctgct tcttgaggac ggatacaatg tttaccagtc gaagcccac      420 ggcctcccgc tgcacctgcc agggaacaag tccccacacc gggaccctgc accccgagga     480
ccagctcgct tcctgccact accaggcctg ccccccgcac tcccggagcc acccggaatc     540 ctggccccc agccccccga tgtgggctcc tcggaccctc tgagcatggt gggaccttcc      600
cagggccgaa gccccagcta cgcttcctga                                      630
```